United States Patent [19]

Sayag et al.

[11] Patent Number: 5,715,292
[45] Date of Patent: Feb. 3, 1998

[54] DIGITAL SENSOR CASSETTE FOR MAMMOGRAPHY

[75] Inventors: Michel Sayag, Mountain View, Calif.; Andrew Karellas, Auburn, Mass.

[73] Assignees: Loral Fairchild Corporation, Syosset, N.Y.; University of Massachusetts Medical Center, Worcester, Mass.

[21] Appl. No.: 344,957

[22] Filed: Nov. 25, 1994

[51] Int. Cl.⁶ ............................................. G01T 1/20
[52] U.S. Cl. .................... 378/98.8; 378/37; 250/368; 250/370.11
[58] Field of Search .................. 378/98.8, 98, 167, 378/182, 37, 98.3; 250/368, 370.09, 370.11

[56] References Cited

U.S. PATENT DOCUMENTS

| | | | |
|---|---|---|---|
| 4,179,100 | 12/1979 | Sashin et al. | 250/416 |
| 4,901,336 | 2/1990 | Nishiki | 378/98.8 |
| 4,905,265 | 2/1990 | Cox et al. | 378/98.8 |
| 4,946,238 | 8/1990 | Sashin et al. | 350/96.27 |
| 4,996,413 | 2/1991 | McDaniel et al. | 250/208.1 |
| 5,008,547 | 4/1991 | Molteni et al. | 250/368 |
| 5,037,207 | 8/1991 | Tomei et al. | 356/444 |
| 5,109,159 | 4/1992 | Hagiwara et al. | 250/368 |
| 5,140,162 | 8/1992 | Stettner | 250/370.09 |
| 5,142,557 | 8/1992 | Toker et al. | 378/37 |
| 5,331,166 | 7/1994 | Yamamoto et al. | 250/370 |
| 5,331,961 | 7/1994 | Inaba et al. | 128/659 |
| 5,340,988 | 8/1994 | Kingsley et al. | 250/370.09 |
| 5,391,879 | 2/1995 | Tran et al. | 250/367 |
| 5,444,756 | 8/1995 | Pai et al. | 378/98.8 |
| 5,510,623 | 4/1996 | Sayag et al. | 378/98.8 X |
| 5,554,850 | 9/1996 | Hejazi | 250/370.11 X |
| 5,563,414 | 10/1996 | Sklebitz | 250/370.11 |
| 5,596,200 | 1/1997 | Sharma et al. | 378/37 X |

FOREIGN PATENT DOCUMENTS

| | | |
|---|---|---|
| 0 296 737 A1 | 12/1988 | European Pat. Off. . |
| 0 603 709 A2 | 6/1994 | European Pat. Off. . |
| 1 254888 A | 11/1989 | Japan . |
| WO92/14169 | 8/1992 | WIPO . |

*Primary Examiner*—David P. Porta
*Attorney, Agent, or Firm*—Perman & Green, LLP

[57] ABSTRACT

A CCD-scintillator x-ray image sensor (18) has a high sensitivity at room temperature and a low profile, enabling the use of the x-ray image sensor in most modern mammography x-ray machines. A cassette 10 that encloses the CCD-based x-ray image sensor has the approximate dimensions of 10.5×7.7×0.6 inches, and is thus form and fit compatible with conventional film-based cassettes. An electronic interface to the cassette requires but a single cable (24) and a standard connector (22) for connection to a CCD sensor electronics unit. The CCD sensor electronics unit interfaces to a computer, such as a conventional personal computer or workstation, having a relatively high resolution display and a provision for digitally recording high-resolution electronic images. The high sensitivity at ambient (room) temperature results from an x-ray scintillator screen (18c) that is coupled to the CCD image sensor (18a) via a bias cut fiber optic faceplate (18b). The CCD image sensor has very low dark current density, high responsivity to the green fluorescence of the screen, and multiple output ports for minimizing the time required for readout and for minimizing the noise bandwidth at the output.

16 Claims, 7 Drawing Sheets

DIGITAL SENSOR CASSETTE FOR MAMMOGRAPHY

FIELD OF THE INVENTION

This invention relates generally to radiography and, in particular, to radiographic techniques employed for mammography.

BACKGROUND OF THE INVENTION

FIG. 1a is an elevational view of a conventional x-ray film cassette 1 used for mammography. The cassette 1 has a hinged top cover 2 and a bottom portion 3. The top cover 2 includes a screen 4 that is responsive to x-rays for converting at least a portion thereof into light, typically ultraviolet or visible light, which then sensitizes a photographic film 5. During use the top cover 2 is closed, and an object to be x-rayed is interposed between the outer surface of the top cover and a source of x-rays. Those x-rays that are not absorbed within the object pass through the top cover and impinge on the screen 4. The screen 4 converts (ideally) all of the impinging x-rays to light which then exposes the film 5. The cassette 1, when closed, has the approximate dimensions of 10.5×7.7×0.6 inches.

Conventional screens 4 use a phosphor such as $CaWO_4$, a broad-band emitter in the uv-blue region of the spectrum. However, rare-earth-activated phosphors allow the x-ray dose to be reduced by at least a factor of four. In order to be useful as an x-ray phosphor, the host matrix of the screen 4 should have a high x-ray absorption and contain an activator that emits efficiently in the blue or green region to match the spectral sensitivity of the film 5. The following combinations have been used for this purpose: GdOS:Tb(III), LaOS:Tb(III), LaOBr:Tb(III), LaOBr:Tm(III), and $Ba(F,Cl)_2$:Eu(II).

Referring to FIG. 1b, it has been known to use electronic light sensors 6 instead of the conventional film-based system shown in FIG. 1a. However, for a digital mammography application the low fabrication yields and costs of large arrays of Charge Coupled Devices (CCDs) have led researchers to resort to tapered fiber optic bundles 7, or minifiers, comprised of either large single bundles or arrays of bundles, with a demagnification of typically approximately 2.5×. The tapered fiber optic bundles are used to convey light from an x-ray screen 9 (shown partially cut-away) to the active surface of a smaller CCD array 8. The reduction in CCD area, due to the taper, is typically a factor of approximately 6.25. While the tapered fiber bundle approach is a viable technique, the overall dimensions (for example, 3×3×1 inches) of the tapered light sensor assembly has precluded the possibility of implementing the much more desirable cassette-type of sensor. That is, the use of the tapered light sensor assembly approach does not yield an electronic imaging system that is physically compatible with the conventional cassettes (FIG. 1a) used in most x-ray machines.

Furthermore, the dark current density of conventional CCDs at room temperature has traditionally required that the CCD array 8 be cooled during use. When used with tapered fiber bundles, even a moderately low profile thermoelectric (TE) cooled CCD array increases the vertical dimension of the sensor assembly by some significant amount. Another problem associated with TE coolers is that there tends to be a large heat load to remove from the back surface of the CCD focal plane assembly. As such, the requirement to also cool the CCD array 8 to reduce the dark current even further complicates the use of CCDs with conventional x-ray machines.

OBJECTS OF THE INVENTION

An object of the present invention is to provide a digital sensor apparatus for x-ray radiation.

Another object of the present invention is to provide a digital sensor apparatus for x-ray radiation including a CCD image sensor.

Still another object of the present invention is to provide a digital image sensing apparatus for mammography.

A further object of the present invention is to provide a digital image sensing apparatus for mammography having a high sensitivity at room temperature.

A still further object of the present invention is to provide a digital image sensing apparatus including an x-ray scintillator screen in combination with a CCD image sensor and contained in a compact cassette housing.

SUMMARY OF THE INVENTION

The foregoing and other problems are overcome, and the objects of the invention are realized, by a CCD-scintillator x-ray image sensor having high sensitivity at room temperature and a low profile, enabling the use of the x-ray image sensor in most modern mammography x-ray machines. A cassette housing that encloses the CCD-based x-ray image sensor has the approximate dimensions of b 10.5×7.7×0.6 inches and is thus form and fit compatible with conventional film-based cassettes.

The electronic interface to the cassette requires but a single cable and a standard connector for connection to a CCD sensor electronics unit. The CCD sensor electronics unit interfaces to a computer, such as a conventional personal computer or workstation, having a relatively high resolution display and a provision for digitally recording high-resolution electronic images.

The high sensitivity at room temperature results from an x-ray scintillator screen that is coupled to the CCD image sensor via a bias cut fiber optic faceplate. The CCD image sensor has very low dark current density, high responsivity to the green fluorescence of the screen, and multiple output ports for minimizing the time required for readout and for minimizing the noise bandwidth at the output.

A first preferred embodiment includes a single, large CCD sensor chip having an active area bounded by sides of approximately 66 mm×60 mm. The CCD sensor chip internally provides 15×15 micron pixels that can be combined through pixel binning techniques to yield effective 30×30 micron pixels or 60×60 micron pixels. The CCD sensor chip is capable of operation in a Multi-Phase Pinned (MPP) low-dark-current mode. Four low-noise preamplifiers can be used, each simultaneously reading out a quadrant of the CCD sensor chip at high speed. The preamplifiers have a scale factor of approximately 3 µV/e-. The CCD sensor chip is coupled to the x-ray sensitive screen via a fiber optic faceplate that also provides x-ray attenuation, thereby minimizing direct x-ray excitation in the CCD sensor chip. Direct excitation is preferably avoided in that it degrades image quality, and may also reduce the useful life of the CCD sensor chip.

The fiber optic faceplate is cut on a bias so that the amount of x-ray radiation is minimized which can pass through the less-attenuating matrix glass that surrounds the fiber optics, and further has EMA (optical attenuation in the matrix glass) which minimizes veiling glare from the fiber optic itself. In a presently preferred embodiment the fiber optic faceplate is approximately 0.18 inch thick, thereby providing a low profile while also providing an adequately low level of veiling glare, an adequate amount of x-ray stopping power, and a relatively low cost.

Support electronics within the electronic cassette provides all required CCD clocks and dc voltage levels, and further includes a plurality of A/D converters, individual ones of which convert the output of one of the preamplifiers to an n-bit digital signal. The support electronics also programs the CCD to operate in one of a number of selectable resolution modes (pixel binning modes). A cable connects the support electronics to the external computer and conveys a standard high throughput bus, preferably a standard SCSI-type bus.

Other and further features, advantages and benefits of the invention will become apparent in the following description taken in conjunction with the following drawings. It is to be understood that the foregoing general description and following detailed description are exemplary and explanatory but are not to be restrictive of the invention. The accompanying drawings which are incorporated in and constitute a part of this invention and, together with the description, serve to explain the principles of the invention in general terms. Like numerals refer to like parts throughout the disclosure.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

Figure 2:
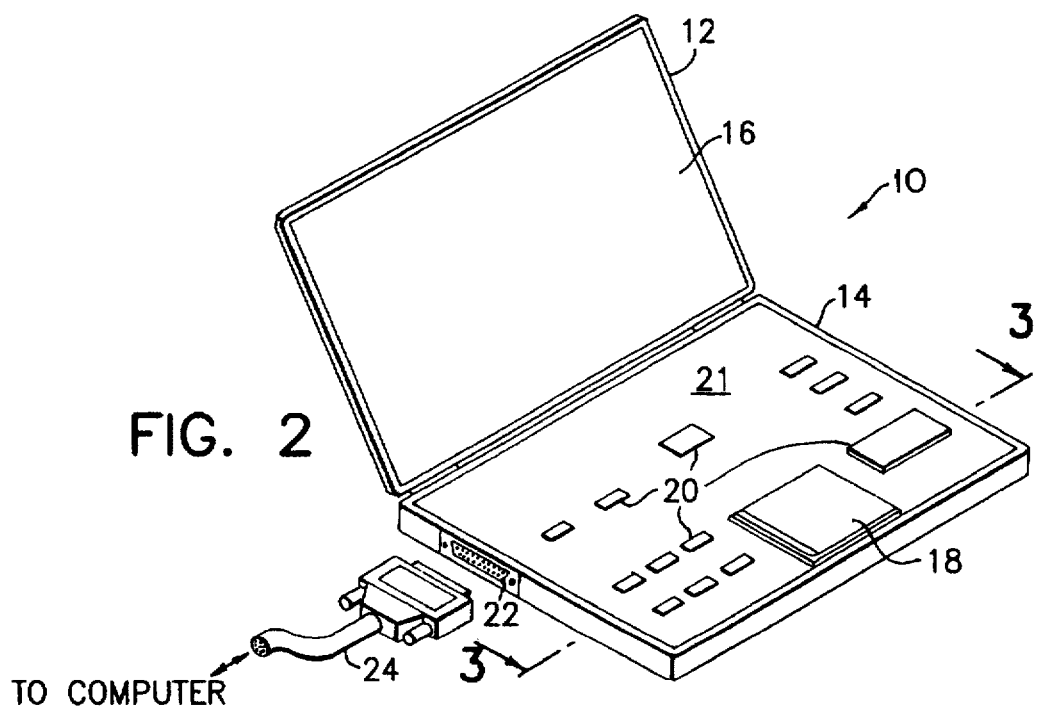
FIG. 2 is an elevational view illustrating an electronic x-ray cassette of this invention in an opened position.

Reference is now made to FIG. 2 for showing an elevational view of a first embodiment of a low profile electronic cassette 10 of this invention. The cassette 10 is shown in an opened position, wherein a hinged top cover is separated from a lower cover 14. The top cover 12 has an inner surface 16 and is substantially transparent to x-rays having energies employed for conventional diagnostic purposes, such as those used in mammography applications. One suitable material for at least the top cover 12 is a carbon fiber based material. In this embodiment the lower cover 14 encloses a circuit board 21 that supports a screen/fiber optic/CCD (SFOCCD) assembly 18. This is considered to be a small field embodiment, and the top, x-ray responsive surface area of the SFOCCD assembly 18 has linear dimensions of approximately 6 cm×6 cm. The circuit board 21 also has mounted thereon a plurality of SFOCCD assembly support circuits 20 and a standard D shell-type connector 22 that interfaces to one end of an interface cable 24. A second end of the cable 24 is coupled to a computer (not shown in FIG. 2), as will be described in further detail below.

Figure 3:
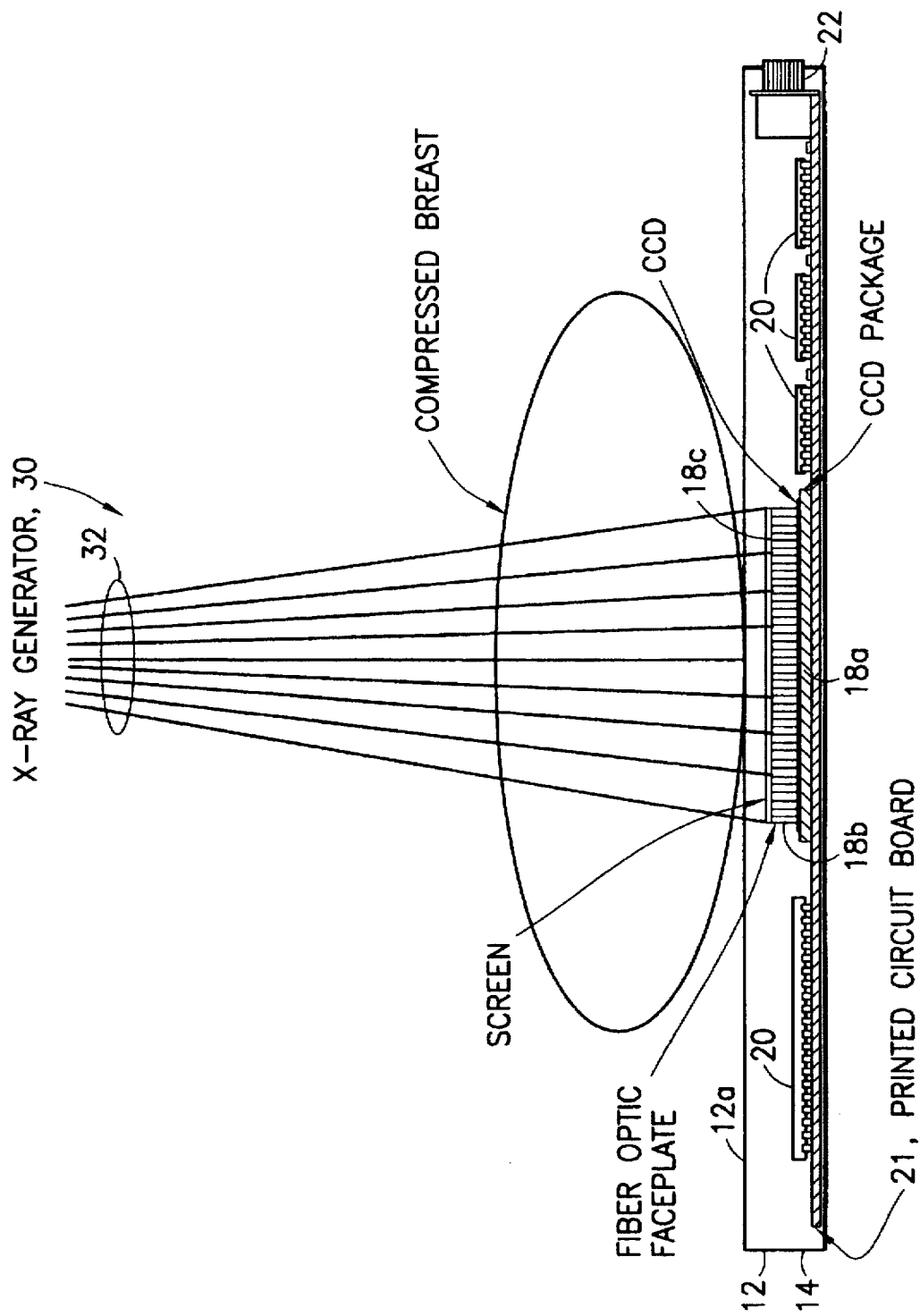
FIG. 3 is a cross-sectional view of the electronic x-ray cassette of FIG. 2 in a closed position when installed within an x-ray machine.

FIG. 3 illustrates a cross-sectional view of the electronic cassette 10 taken along the section line 3—3 of FIG. 2, and with the top cover 12 closed and the cassette 10 installed within an x-ray machine having an x-ray generator 30 providing an x-ray beam 32. An object to be x-rayed, in this case a breast, is positioned over a top surface 12a of the top cover 12. The breast is compressed against or over the top cover 12a in accordance with conventional practice, and is positioned such that it lies between the beam 32 and the top surface of the SFOCCD assembly 18.

The SFOCCD assembly 18 is comprised of a large area CCD sensor chip 18a, over which is bonded a fiber optic faceplate 18b, over which is bonded an x-ray sensitive screen 18c.

In this embodiment the SFOCCD assembly 18 has an active area bounded by sides of approximately 60 mm×60 mm. The CCD sensor chip 18a internally provides a 4K by 4K array of 15×15 micron pixels, which can be combined on chip though pixel binning operations to provide an effective 2K by 2K array of 30×30 micron pixels or an effective 1K by 1K array of 60×60 micron pixels. The CCD sensor chip 18a is capable of operation in the MPP low-dark-current mode, and employs a basic three phase clock that transitions between approximately −10V to +5V.

Figure 7:
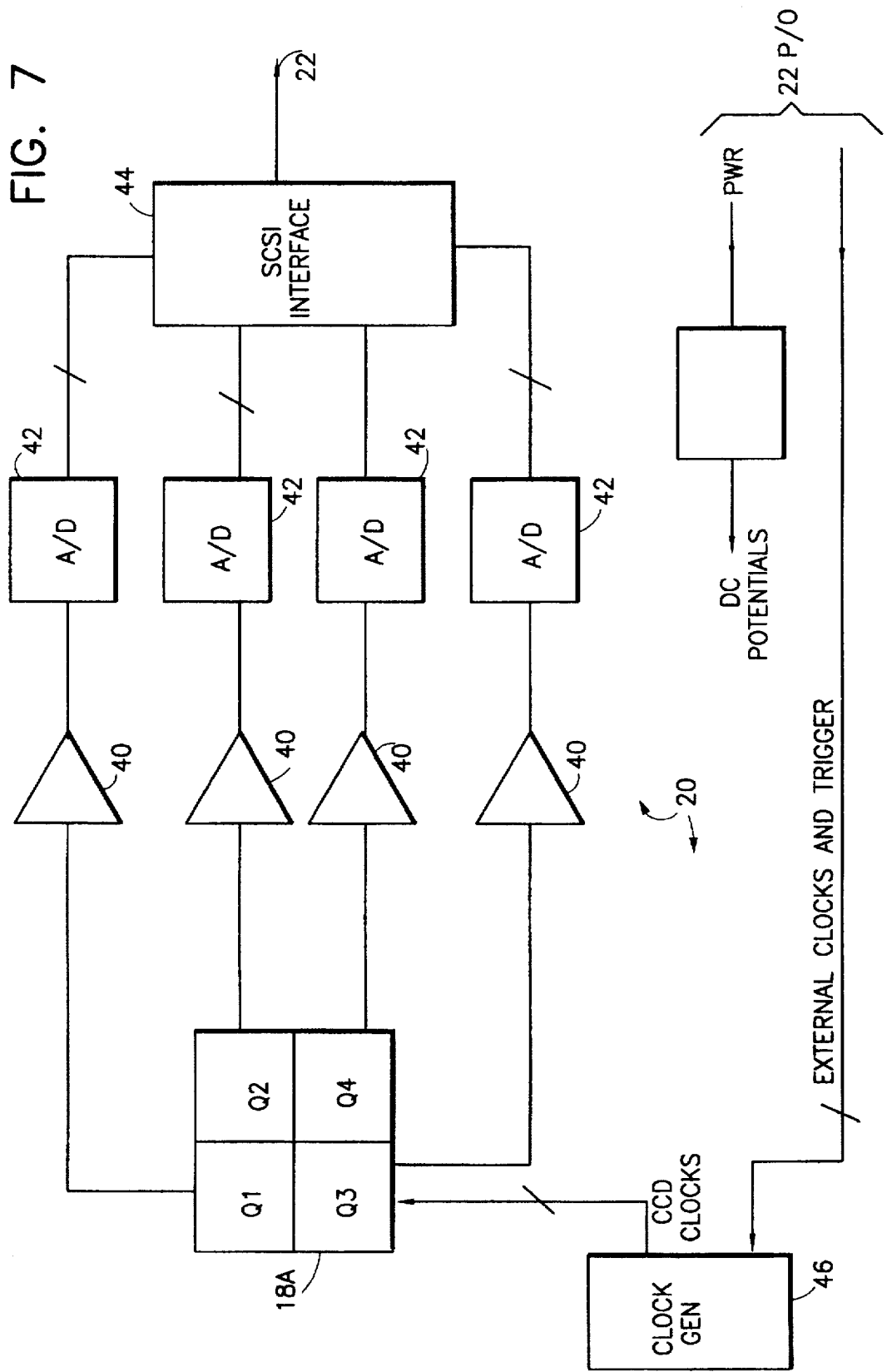
FIG. 7 is a simplified block diagram of the CCD sensor chip and support electronics of the embodiments of either FIGS. 3 or 5.

Referring also now to FIG. 7, in a presently preferred embodiment the CCD sensor chip 18a is electrically differentiated into quadrants (Q1–Q4), each of which has a low noise preamplifier 40 for reading out of the CCD sensor chip 18a the photo-induced charge resulting from the conversion of x-rays into visible light in the screen 18c. The use of multiple preamplifiers enables the charge to be read out a high speed, thereby reducing the effect of any dark currents generated after an x-ray exposure (it being realized that the CCD sensor chip 18a is preferably not cooled, but is instead operated at ambient temperature). The preamplifiers 40 have a scale factor of approximately 3 µV/e-. The outputs of the preamplifiers 42 are input to associated A/D converters 42. Each of the A/D converters 42 provides a 12-bit digital representation of the voltage corresponding to the accumulated charge within individual ones of the CCD pixels. The outputs of the A/D converters 42 are provided to a suitable interface device, in this case a SCSI interface device 44, which outputs the A/D converter signals via the connector 22 and cable 24 to the external data processor. A clock generator 46 provides the required clocks and control signals for reading out the accumulated charge and otherwise operating the CCD sensor chip 18a. The support electronics 20 is also capable of operating CCD sensor chip 18a in one of a number of selectable resolution modes (for example, in a 2×2 pixel binning mode). In pixel binning sets of charge packets are grouped or combined on-chip before being read-out and sensed. Using this technique, and as was noted above, the SFOCCD assembly 18 is capable of being configured to operate with various resolutions that include a 1K by 1K pixel mode, a 2K by 2K pixel mode, and a 4K by 4K pixel mode. The SFOCCD assembly 18 is capable of collecting and outputting multiple images per second.

The support electronics further includes circuitry 48 for providing all required DC operating potentials and power supplies from power leads that form a portion of the cable 24. External clocks and a trigger signal (described below) are also conveyed through the cable 24 and connector 22.

Figure 8:
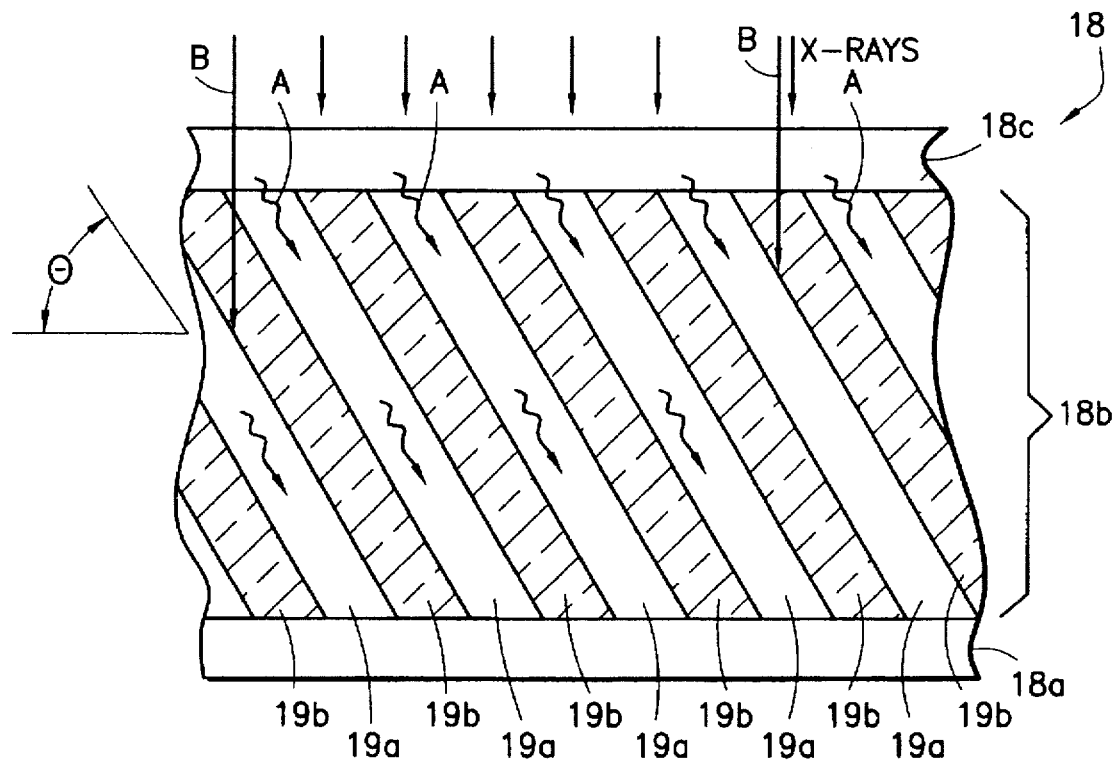
FIG. 8 is a cross-sectional view through a portion of the low profile CCD sensor assembly used in either of the embodiments of FIGS. 3 and 5.

Referring now also to the cross-sectional view (not to scale) of FIG. 8, the CCD sensor chip 18a is coupled to the x-ray sensitive screen 18c via the fiber optic faceplate 18b which also provides x-ray attenuation, thereby minimizing direct x-ray excitation in the CCD sensor chip 18a. Direct excitation of the CCD sensor chip 18a is preferably avoided in that it degrades image quality, and may also reduce the useful life of the CCD sensor chip.

The fiber optic faceplate 18b is cut on a bias (indicated by the angle θ, for example, 6°–7°) so that the amount of x-ray radiation is minimized which can pass through the less-attenuating matrix glass 19b that surrounds the fiber optics 19a. The x-ray attenuation is indicated by the x-rays labeled B in FIG. 8, which are seen to be absorbed by the bias cut fiber optics 19a. The fiber optic faceplate 18b further has extra-mural absorption (EMA), that is, optical attenuation in the matrix glass to minimize veiling glare from the fiber optics 19a. In a presently preferred embodiment the bias cut fiber optic faceplate 18b is approximately 0.18 inch thick, thereby providing a low profile while also providing an adequately low level of veiling glare, an adequate amount of x-ray stopping power, and a relatively low cost. Electromagnetic radiation that is generated in the screen 18c (typically light having wavelengths in the green portion of the spectrum) is guided through the fiber optics 19a (as indicated by the arrows designated A) to the radiation responsive top surface of the CCD sensor chip 18a.

The screen 18c can be a conventional x-ray responsive screen material, such as one known in the art as MINR that is available from Kodak. In general, the screen 18c is preferably comprised of one or more high efficiency x-ray phosphor materials, such as the GdOS:Tb(III), LaOS:Tb (III), LaOBr:Tb(III), LaOBr:Tm(III), and Ba(F,Cl)$_2$:Eu(II) materials referred to previously.

Figure 1A:
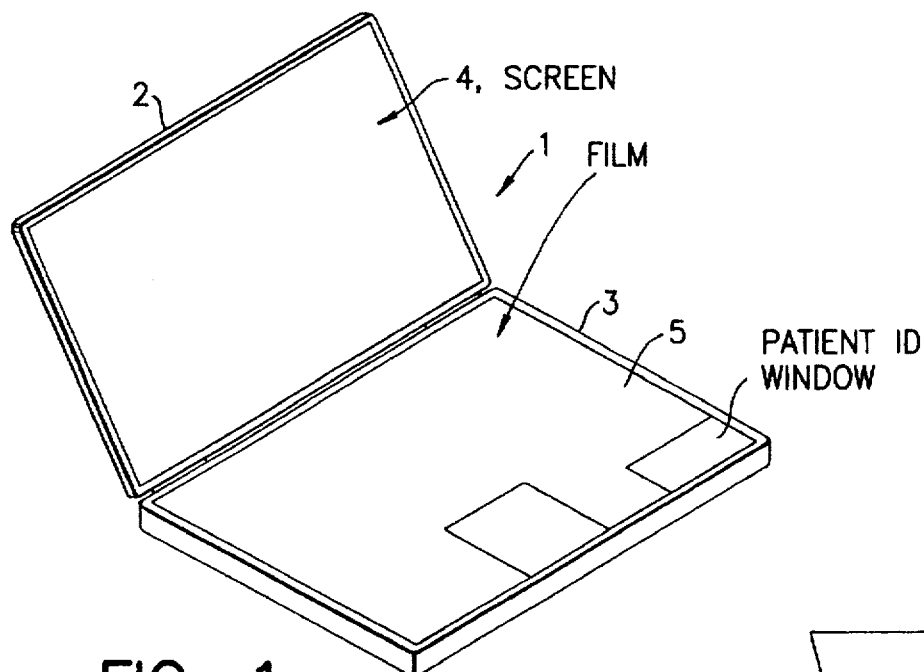
FIG. 1a is an elevational view showing a conventional x-ray film cassette in an opened position.

The screen 18c, fiber optic faceplate 18b, and CCD sensor chip 18a are bonded together with a conventional transparent optical cement to form the SFOCCD assembly 18. Due to the relatively small overall thickness of the SFOCCD assembly 18, as contrasted with the tapered fiber optic minifiers of the prior art, the cassette 10 enclosing the SFOCCD assembly 18 and support electronics 20 can have the approximate dimensions of 10.5×7.7×0.6 inches, and is thus form and fit compatible with conventional film-based cassettes of a type illustrated in FIG. 1a.

Figure 1B:
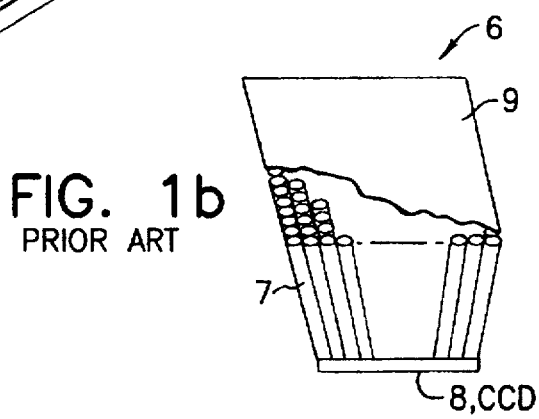
FIG. 1b is an elevational view illustrating a conventional tapered fiber optic CCD sensor.

Furthermore, it should be noted that due to the relative thinness of the faceplate 18b that a substantially 1:1 imaging ratio is obtained between the top surface of the faceplate 18b and the radiation receiving surface of the large CCD sensor chip 18a. This is clearly different than the approximately 2.5:1 ratio obtained with the conventional minifier shown in FIG. 1b.

Figure 4:
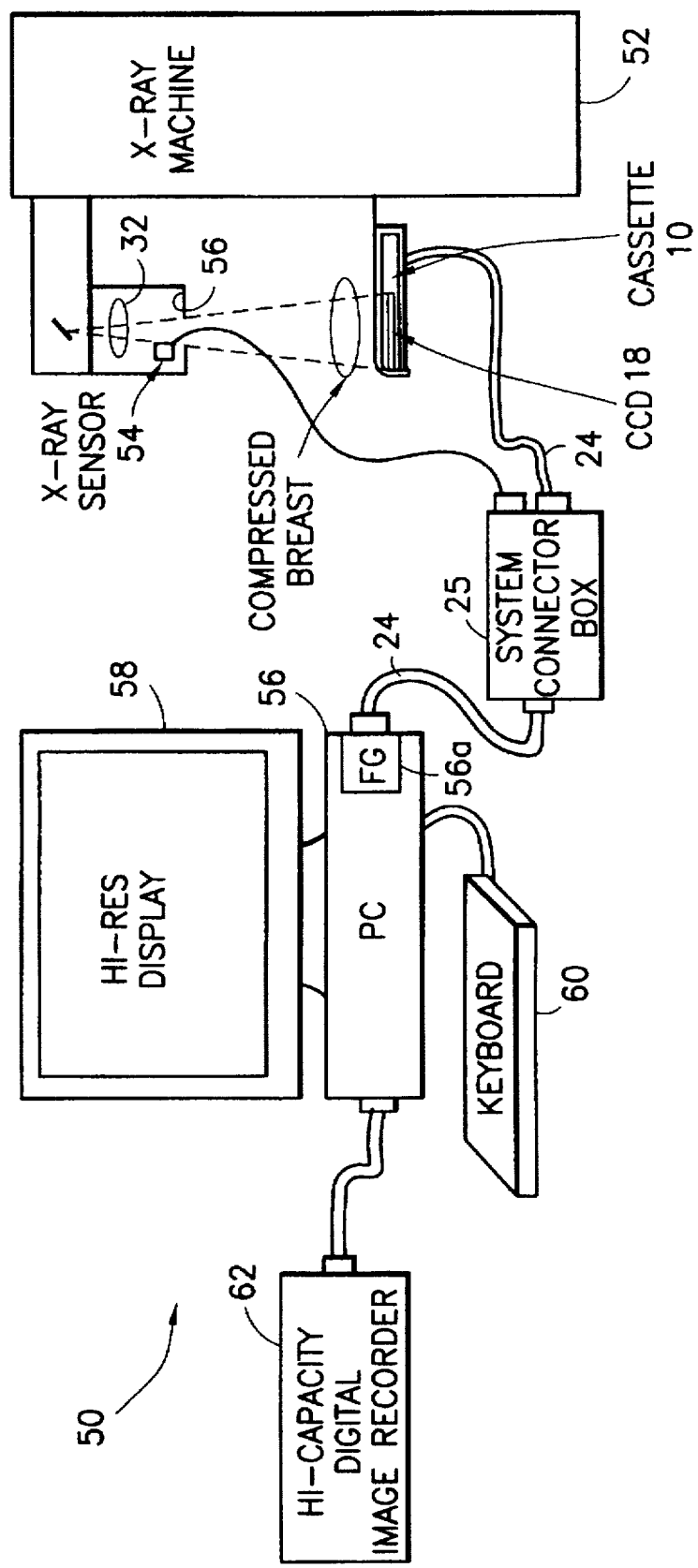
FIG. 4 is a block diagram of an x-ray system in accordance with this invention.

FIG. 4 is a block diagram of an x-ray system 50 in accordance with this invention. Although illustrated in the context of an x-ray system used for a mammography application, including stereotactic needle core biopsy, pre-operative localization, and spot view mammography applications, it should be realized that the x-ray system 50 using the novel electronic cassette 10 of this invention is capable of other uses, including industrial inspection, process control, and a variety of small field medical x-ray applications.

A conventional x-ray machine 50 generates the x-ray beam 32 which passes through the breast to the cassette 10. A portion of those x-rays that are not absorbed within the breast are converted to light in the screen 18c, the light is guided through the bias cut fiber optic faceplate 18b, and is detected by the CCD sensor chip 18a. The CCD pixel image data is read-out and provided through the cable 24, via an optional system connector box 25, to a data processor, such as a PC or a workstation 56. The PC 56 includes a high resolution display 58, a keyboard 60, and an optional high capacity digital image recorder 62 used for archival and playback purposes. The PC 56 runs suitable image processing software for displaying the CCD-generated image. The PC 56 includes a conventional frame grabber (FG) 56a that is capable of capturing and storing images of up to 12-bit signal level resolution and up to 2048×2048 pixel resolution. Programs for digitally enhancing the image are provided as required by the operator or radiologist. Image zooming and other image manipulation functions are also provided as required.

As is apparent in FIG. 4, the electronic cassette 10 of this invention is form and fit compatible with a conventional film cassette, and can thus be installed within the x-ray machine 50 without requiring any physical or electrical modifications.

The system connector box 25 also connects to an x-ray sensor 54 that mounts inside of the aperture-defining baffle 56 of the x-ray machine 52. The x-ray sensor 54 is located where it can sense a substantial x-ray signal level with approximately the first one percent of the lowest exposure level, and where it can do so without occluding any of the imaging x-ray beam path. The x-ray sensor 54 may be attached by any one of several convenient means such as a clip, a magnet, etc., so as not to require any modifications to the x-ray machine 50. One suitable embodiment for the x-ray sensor 50 is a reverse biased Schottky-type diode, wherein an increase in leakage current that is induced by the x-ray flux is detected. The detected leakage current signal is employed as a trigger and gating signal to the support electronics 50.

Figure 9:
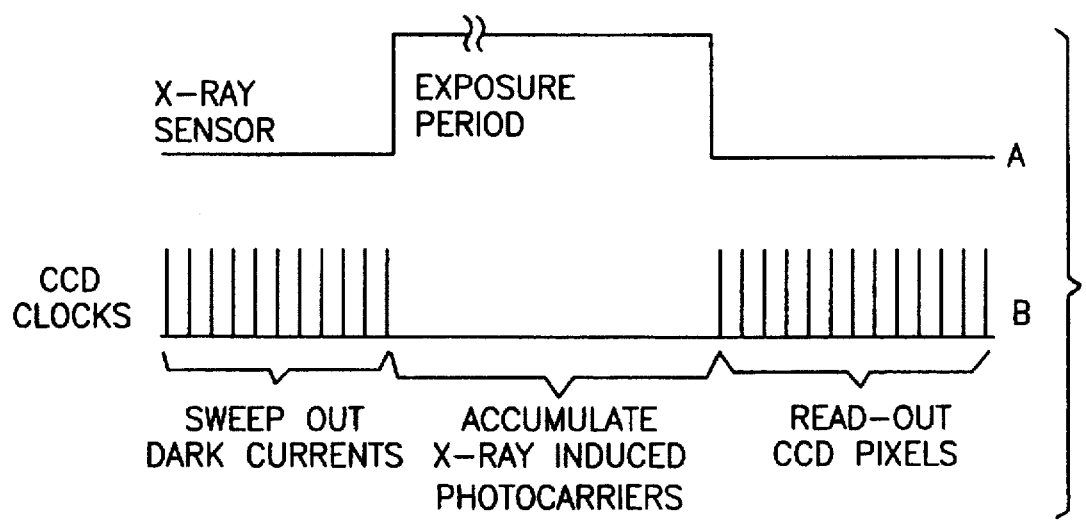
FIG. 9 is a timing diagram illustrating the application of read-out clocks to the low profile CCD sensor assembly before, during and after an exposure.

In this regard reference is now made to the exemplary timing diagram of FIG. 9. Trace A depicts the output of the x-ray sensor 54, which is shown as being asserted during an x-ray exposure period. A typical duration for the exposure period during a mammography examination is approximately one second. Before the exposure period the clock generator 46 (FIG. 7) operates to generate CCD read-out clocks (trace B) that are used to sweep out any dark current charge that accumulates within the CCD pixels. During the exposure period the CCD clocks are stopped, and the photo-induced charge allowed to accumulate. The magnitude of the charge on a given pixel is a function of the x-ray flux reaching the overlying portion of the screen 18c, which is in turn a function of the tissue density of a corresponding overlying portion of the breast. At the end of the exposure period, as indicated by the output signal from the x-ray sensor 54 being deasserted, the CCD clocks are restarted so as to rapidly read-out the accumulated charge before a significant post-exposure dark current can accumulate. The use of the multiple preamplifiers 40 and A/D converters 42 facilitates the rapid read-out of the exposure-related charge.

Figure 5:
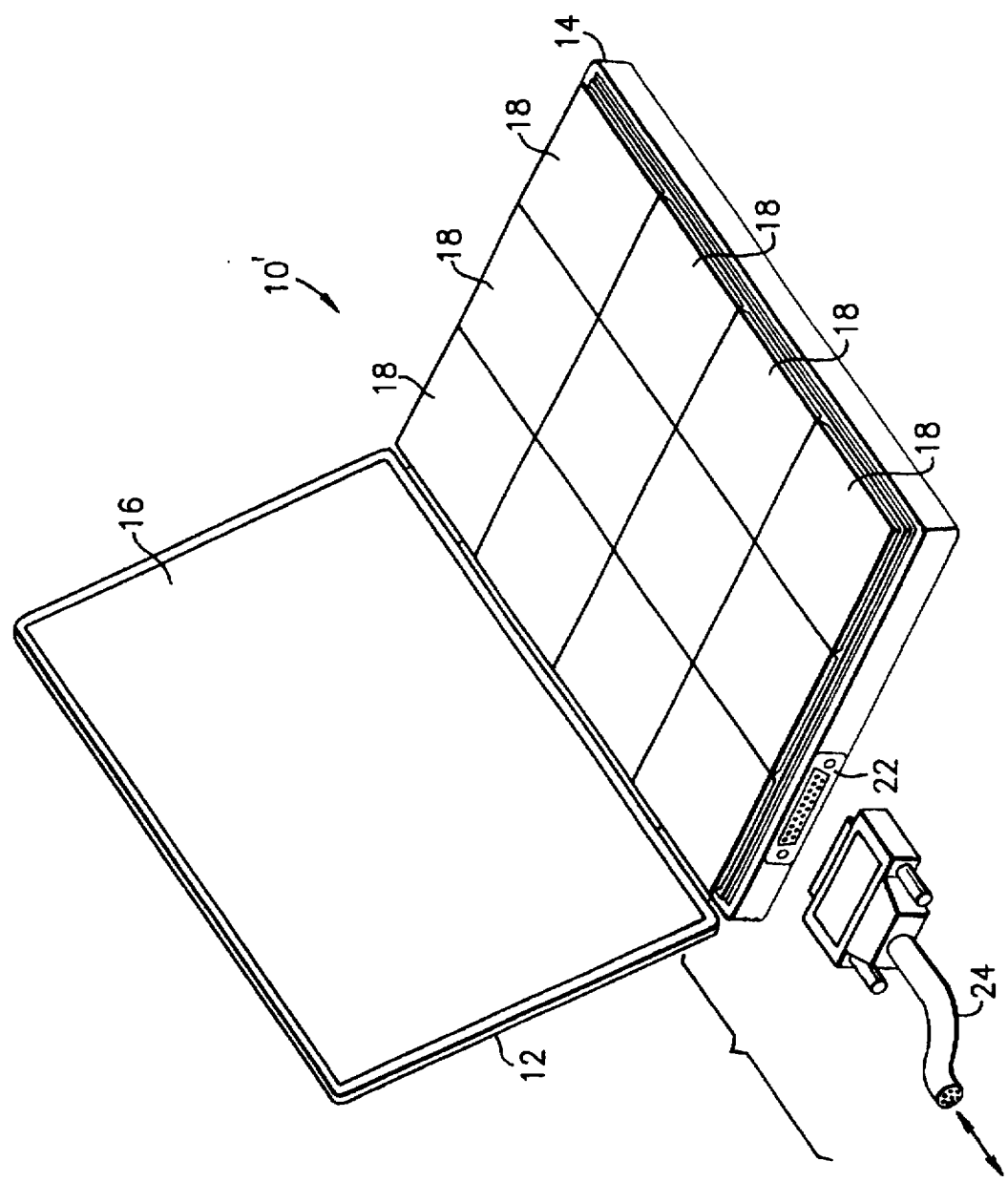
FIG. 5 is an elevational view illustrating a second, full field, embodiment of an electronic x-ray cassette of this invention in an opened position.
Figure 6:
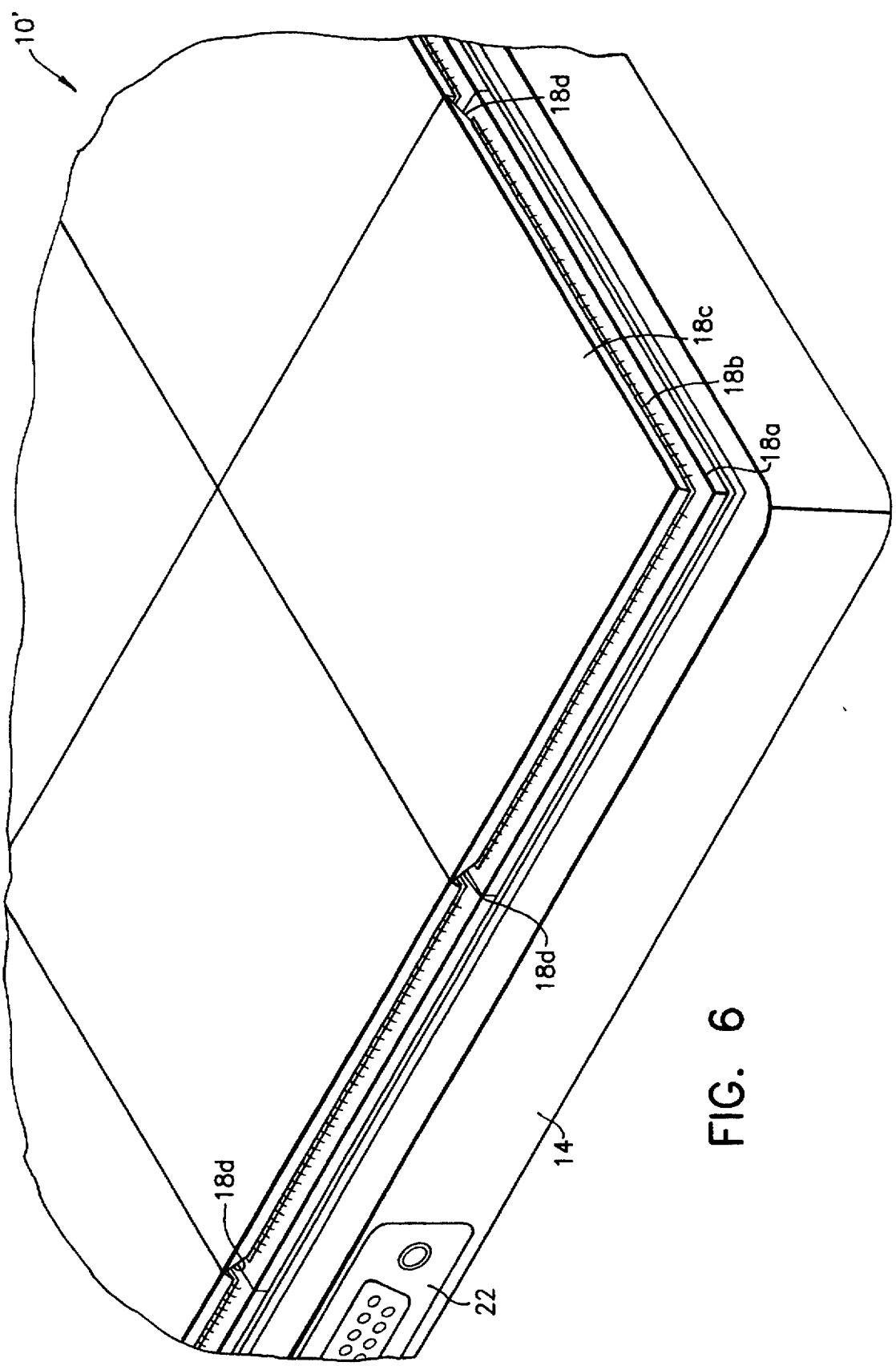
FIG. 6 is an enlarged elevational view showing the full field electronic x-ray cassette of FIG. 5.

FIGS. 5 and 6 illustrate a further embodiment of this invention wherein a plurality (e.g., 12) of the large 6 cm×6 cm SFOCCD assemblies 18 are installed within a full field electronic cassette 10'. The full field electronic cassette 10' has overall dimensions, when closed, of approximately 10.5×7.7×0.6 inches, and is thus form and fit compatible for the conventional film-based cassette of FIG. 1a.

The multiple SFOCCD assemblies 18 are constructed with fiber optic faceplates 18b that are bias cut so that the input and output image planes are displaced laterally by approximately 1 mm to 2 mm, as indicated by the sloping edges 18d in FIG. 6. This allows for closely abutting the SFOCCD assemblies 18 into a mosaic CCD array which has a minimum of "dead space", i.e., non-imaging regions, at the seams between the SFOCCDs. Each SFOCCD assembly 18 may be provided with the multiple preamplifiers 40 and A/Ds 42, which in this case are preferably mounted on the reverse side of the printed circuit board 21. Using this approach the total separation at the scintillator (e.g., between adjacent scintillator screens 18c) can be 20–40 microns or less.

While the invention has been particularly shown and described with respect to presently preferred embodiments thereof, it will be understood by those skilled in the art that changes in form and details may be made therein without departing from the scope and spirit of the invention. For example, in other embodiments of the invention the x-ray sensor 54 of FIG. 4 can be located within the cassette 10, thereby even further simplifying the interface to the x-ray machine. In this case it may be desirable to use the CCD sensor itself for detecting the onset and termination of the x-ray exposure period. It is also within the scope of this invention to input to the cassette a predetermined exposure time, and to thus begin the readout of the CCD pixels after delaying for this period of time after detecting the initiation of the x-ray exposure. Also, in other embodiments of the invention the screen 18b can be replaced by other suitable scintillating materials and formats, such as by a layer of suitable x-ray phosphor material that is deposited directly upon or over a top surface of the bias cut fiber optic faceplate 18b. By example, an evaporated layer of a cesium iodide-based material may be suitable for this purpose. It is also within the scope of this invention to embed a suitable x-ray phosphor material into a surface of the fiber optic faceplate. One technique for accomplishing this is to etch the surface of the fiber optic faceplate to create voids, and to then fill the voids with the desired scintillating material.

It should thus be apparent that the scope of the teaching of this invention is not intended to be limited by only the embodiments that have been expressly disclosed and illustrated, but that instead the scope of the teaching of this invention should be read as being commensurate with the scope of the claims that follow.

What is claimed is:

1. An imaging device, comprising:
   a region comprised of a material that is responsive to incident x-ray radiation for converting at least a portion of the incident x-ray radiation into light;
   a two dimensional light sensor array having a radiation receiving surface containing charge coupled device light sensors; and
   a bias cut fiber optic faceplate interposed between a bottom surface of the region and said radiation receiving surface of the array for guiding the light to the charge coupled device light sensors with a substantially 1:1 imaging ratio and minimizing a distance between said radiation receiving surface and said bottom surface of said region; wherein
   said device is installed within a housing; and wherein
   said housing has dimensions that are form and fit compatible with an x-ray film cassette of a type that is installable within an x-ray machine for use in mammographic imaging.

2. An imaging device as set forth in claim 1 wherein said device has a total thickness that enables said device to be installed within said housing which has a total thickness of approximately 0.6 inch.

3. An imaging device as set forth in claim 2 wherein said housing has at least one wall that is substantially transparent to the incident x-rays.

4. An imaging device as set forth in claim 1 wherein said housing also contains at least one amplifier for reading out a light-induced charge from individual ones of said charge coupled device light sensors, said housing further containing at least one A/D converter for converting electrical signals representative of the read-out light induced charge to digital representations of the electrical signals and means for coupling an output of said at least one A/D converter to a cable for conveying said outputs to a remotely located data processor.

5. A method of obtaining an x-ray mammographic image, comprising the steps of:
   providing an electronic cassette containing an uncooled two dimensional CCD array having a radiation receiving surface that is optically coupled to an output of a material that is responsive to x-ray radiation that passes through a breast for converting the x-ray radiation into electromagnetic radiation having wavelengths that are suitable for conversion into photo-induced charge by pixels of the CCD array, the electronic cassette having dimensions that are form and fit compatible with an x-ray film cassette of a type that is used for mammographic imaging;
   generating clocking pulses for reading out dark current charge from the pixels of the CCD array;
   generating a signal for indicating a beginning of an x-ray exposure of the object; in response to the generation of the signal, terminating the generation of the clocking pulses during the x-ray exposure so as to enable the accumulation of photo-induced charge within the pixels of the CCD array;
   in response to a termination of the x-ray exposure, initiating the generation of the clocking pulses; and
   reading out the photo-induced charge from the pixels of the CCD array; wherein the CCD array is partitioned into a plurality of sub-arrays, and wherein the step of reading out the photo-induced charge reads out the charge in parallel from each of the sub-arrays.

6. An x-ray system including an x-ray source providing an x-ray beam, said x-ray system further comprising:
   x-ray sensor means for generating a signal for indicating a presence of said x-ray beam; and
   an electronic imaging cassette installable within said x-ray beam, said cassette having dimensions that are form and fit compatible with a conventional x-ray film cassette of a type used for mammographic imaging, said cassette having at least one wall that is substantially transparent to said x-ray beam, said cassette containing at least one imaging device comprising;
   scintillating screen means comprised of a material that is responsive to said x-ray beam that passes through said wall for converting at least a portion of the beam into light;
   a two dimensional light sensor array having a radiation receiving surface containing charge coupled device light sensors; and a bias cut fiber optic faceplate interposed between a bottom surface of the screen means and said radiation receiving surface of said array for guiding the light to the charge coupled device light sensors and minimizing a distance between said radiation receiving surface and said bottom surface of said screen means said bias cut fiber optic faceplate relaying light generated by said scintillating screen means to said radiation receiving surface of said two dimensional light sensor array with a substantially 1:1 imaging ratio;

said cassette further comprising, a plurality of amplifier circuits for converting a light-induced charge from individual ones of said charge coupled device light sensors into representative voltages;

a plurality of A/D converters for converting the voltages representative of the read-out light induced charge into digital representations of the voltages;

means for coupling outputs of said A/D converters to a remotely located image display means; and timing circuit means operable for generating timing signals for said array for controlling the read out of the light-induced charge from individual ones of said charge coupled device light sensors, said timing circuit means being responsive to said signal generated by said x-ray sensor means for suspending the generation of said timing signals during a time that said x-ray beam is present.

7. An x-ray system as set forth in claim 6 wherein said image display means includes means for transforming the outputs of said A/D converters to data representing displayable image pixels and for storing said data representing displayable image pixels.

8. A system for obtaining an x-ray mammographic image, comprising:

an electronic cassette containing at least one two dimensional CCD array having a radiation receiving surface that is optically coupled to an output of a material that is responsive to x-ray radiation that passes through a breast for converting the x-ray radiation into electromagnetic radiation having wavelengths that are suitable for conversion into photo-induced charge by pixels of the CCD array, said electronic cassette having dimensions that are form and fit compatible with an x-ray film cassette of a type that is used for mammographic imaging;

means for outputting a signal for indicating a beginning of an x-ray exposure of the object; and means for generating clocking pulses for reading out dark current charge from the pixels of the CCD array, said generating means being responsive to the means for outputting for terminating the generation of the clocking pulses during the x-ray exposure so as to enable the accumulation of photo-induced charge within the pixels of the CCD array, said generating means being further responsive to a termination of the x-ray exposure for initiating the generation of the clocking pulses for reading out the photo-induced charge from the pixels of the CCD array; wherein the CCD array is an uncooled array that is partitioned into a plurality of sub-arrays, and wherein the photo-induced charge is read out in parallel from each of the sub-arrays.

9. A method of obtaining an x-ray mammographic image, comprising the steps of:

providing an electronic cassette containing an uncooled two dimensional CCD array having a radiation receiving surface that is optically coupled to an output of a material that is responsive to x-ray radiation that passes through a breast for converting the x-ray radiation into electromagnetic radiation having wavelengths that are suitable for conversion into photo-induced charge by pixels of the CCD array, the electronic cassette having dimensions that are form and fit compatible with an x-ray film cassette of a type that is used for mammographic imaging;

generating clocking pulses for reading out dark current charge from the pixels of the CCD array;

generating a signal for indicating a beginning of an x-ray exposure of the object;

in response to the generation of the signal, terminating the generation of the clocking pulses during the x-ray exposure so as to enable the accumulation of photo-induced charge within the pixels of the CCD array;

in response to a termination of the x-ray exposure, initiating the generation of the clocking pulses; and reading out the photo-induced charge from the pixels of the CCD array.

10. A method as set forth in claim 9 and further including the steps of:

converting, within the cassette, the read out photo-induced charge to a digital representation of the magnitude of the charge; and transmitting the digital representations from the cassette to a display device for displaying an image corresponding to the read out photo-induced charge.

11. A method as set forth in claim 9 and further including the steps of:

converting, within the cassette, the read out photo-induced charge to a digital representation of the magnitude of the charge; and transmitting the digital representations from the cassette to a digital storage device.

12. A system for obtaining an x-ray mammographic image, comprising:

an electronic cassette containing at least one two dimensional CCD array having a radiation receiving surface that is optically coupled to an output of a material that is responsive to x-ray radiation that passes through a breast for converting the x-ray radiation into electromagnetic radiation having wavelengths that are suitable for conversion into photo-induced charge by pixels of the CCD array, said electronic cassette having dimensions that are form and fit compatible with an x-ray film cassette of a type that is used for mammographic imaging;

means for outputting a signal for indicating a beginning of an x-ray exposure of the object; and means for generating clocking pulses for reading out dark current charge from the pixels of the CCD array, said generating means being responsive to the means for outputting for terminating the generation of the clocking pulses during the x-ray exposure so as to enable the accumulation of photo-induced charge within the pixels of the CCD array, said generating means being further responsive to a termination of the x-ray exposure for initiating the generation of the clocking pulses for reading out the photo-induced charge from the pixels of the CCD array.

13. A system as set forth in claim 12 and further comprising:

means for converting, within the electronic cassette, the read out photo-induced charge to a digital representation of the magnitude of the charge; and means for transmitting the digital representations from the electronic cassette to a digital storage device.

14. A system as set forth in claim 12 and further comprising:

means for converting, within the electronic cassette, the read out photo-induced charge to a digital representation of the magnitude of the charge; and means for transmitting the digital representations from the electronic cassette to a display device for displaying an image corresponding to the read out photo-induced charge.

15. A system as set forth in claim 12 and further comprising a bias cut fiber optic faceplate that is interposed between said material and said radiation receiving surface of said CCD array for guiding the light thereto with a substantially 1:1 imaging ratio.

16. A system as set forth in claim 12 wherein there are a plurality of said uncooled two dimensional CCD arrays that are closely abutted one to another for forming a substantially continuous image corresponding to an x-ray radiation transmission profile of the breast.

* * * * *